United States Patent
Prus et al.

(10) Patent No.: US 10,900,933 B2
(45) Date of Patent: Jan. 26, 2021

(54) PHASED ARRAY CALIBRATION FOR GEOMETRY AND ABERRATION CORRECTION

(71) Applicants: Oleg Prus, Hinanit (IL); Yoav Levy, Hinanit (IL)

(72) Inventors: Oleg Prus, Hinanit (IL); Yoav Levy, Hinanit (IL)

(73) Assignee: INSIGHTEC, LTD, Tirat Carmel (IL)

( * ) Notice: Subject to any disclaimer, the term of this patent is extended or adjusted under 35 U.S.C. 154(b) by 0 days.

(21) Appl. No.: 16/876,757

(22) Filed: May 18, 2020

(65) Prior Publication Data

US 2020/0278327 A1     Sep. 3, 2020

Related U.S. Application Data

(62) Division of application No. 15/837,392, filed on Dec. 11, 2017, now Pat. No. 10,739,316.

(51) Int. Cl.
| | |
|---|---|
| G01N 29/30 | (2006.01) |
| A61B 8/00 | (2006.01) |
| G01S 7/52 | (2006.01) |
| G01F 1/66 | (2006.01) |
| G01N 29/07 | (2006.01) |
| A61B 8/08 | (2006.01) |
| A61B 17/00 | (2006.01) |

(52) U.S. Cl.
CPC ............... *G01N 29/30* (2013.01); *A61B 8/00* (2013.01); *A61B 8/4488* (2013.01); *A61B 8/481* (2013.01); *A61B 8/58* (2013.01); *A61B 8/587* (2013.01); *G01F 1/668* (2013.01); *G01N 29/07* (2013.01); *G01S 7/5205* (2013.01); *G01S 7/52022* (2013.01); *A61B 8/4416* (2013.01); *A61B 2017/00725* (2013.01)

(58) Field of Classification Search
CPC ................................. A61B 8/00; G01N 29/30
See application file for complete search history.

(56) References Cited

U.S. PATENT DOCUMENTS

| | | |
|---|---|---|
| 2007/0106156 A1 | 5/2007 | Altmann et al. |
| 2014/0058266 A1 | 2/2014 | Call et al. |
| 2014/0269209 A1* | 9/2014 | Smith .................. A61B 8/4461 367/140 |
| 2015/0223777 A1* | 8/2015 | Rasoulian ............ A61B 8/4444 600/461 |

(Continued)

OTHER PUBLICATIONS

International Search Report and the Written Opinion for international application No. PCT/IB2018/001350 dated Jun. 3, 2019 17 pages.

*Primary Examiner* — Jamel E Williams
(74) *Attorney, Agent, or Firm* — Morgan, Lewis & Bockius LLP

(57) ABSTRACT

Various approaches for calibrating the geometry of an ultrasound transducer having multiple transducer elements include providing an acoustic reflector spanning an area traversing by multiple beam paths of ultrasound waves transmitted from all (or at least some) transducer elements to a focal zone; causing the transducer elements to transmit the ultrasound waves to the focal zone; measuring reflections of the ultrasound waves off the acoustic reflector; and based at least in part on the measured reflections, determining optimal geometric parameters associated with the transducer elements.

21 Claims, 10 Drawing Sheets

(56) References Cited

U.S. PATENT DOCUMENTS

| | | |
|---|---|---|
| 2017/0023359 A1* | 1/2017 | Prause .................. G01N 29/30 |
| 2017/0112476 A1 | 4/2017 | Belevich et al. |
| 2019/0178851 A1* | 6/2019 | Prus ...................... G01N 29/30 |
| 2020/0022678 A1* | 1/2020 | McLaughlin ........ A61B 8/4254 |
| 2020/0041400 A1* | 2/2020 | Lee ...................... A61B 8/4488 |

* cited by examiner

PHASED ARRAY CALIBRATION FOR GEOMETRY AND ABERRATION CORRECTION

RELATED APPLICATION

This application claims the benefit of and priority to U.S. Patent Application No. 15/837,392, filed on Dec. 11, 2017, the entire disclosure of which is hereby incorporated by reference.

FIELD OF THE INVENTION

The invention relates generally to ultrasound systems and, more particularly, to systems and methods for calibrating transducer geometry and ultrasound aberrations resulting from a medium through which the ultrasound waves travel.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, targeted drug delivery, disruption of the blood-brain barrier (BBB), lysing of clots, and other surgical procedures. During tumor ablation, a piezoceramic transducer is placed externally to the patient, but in close proximity to the tumor to be ablated (i.e., the target region). The transducer converts an electronic drive signal into mechanical vibrations, resulting in the emission of acoustic waves (a process hereinafter referred to as "sonication"). The transducer may be geometrically shaped and positioned along with other such transducers so that the ultrasound energy they emit collectively forms a focused beam at a "focal zone" corresponding to (or within) the target region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

During a focused ultrasound procedure, a series of sonications is applied to cause coagulation necrosis of the target tissue (such as a tumor) without damaging surrounding tissue. To achieve this, ultrasonic energy emitted from the transducer must be accurately and reliably shaped and focused onto the desired target location. Transducer elements that are not properly configured can lead to improper focal qualities, thereby causing ineffective treatment and/or undesired damage to the non-target tissue. In addition, improperly shaped ultrasound beams may generate unexpected, secondary hot spots at locations other than the intended focal zone; such hot spots may lead to undesired heating, pain for the patient, and/or possibly necrosis of non-targeted tissue.

One source of transducer output errors results from geometric imperfections in the transducer elements (i.e., deviations from their expected locations). For example, assuming a transducer is designed to have a spherical shape, the software that drives each transducer element is configured to activate individual transducer elements based on their positioning according to a spherical model or design. To the extent that the actual location of one or more transducer elements is shifted from the expected location during manufacture, use and/or repair, or if the location shifts as a result of, for example, deformation by heat, the result can be permanent focusing errors due to software programmed according to an ideal spherical model.

Another source of transducer output errors is inhomogeneity of the intervening medium (e.g., a fluid or tissue) through which the ultrasound waves travel prior to reaching the focal zone. The ultrasound waves may interact with the medium through multiple processes, including propagation, scattering, absorption, reflection, and refraction. For example, inhomogeneity of the medium may cause refraction of acoustic energy at the boundaries of regions that have different speeds of sound. Refraction may decrease constructive interference, and hence, the intensity of the acoustic energy at the focal zone. Thus, an inhomogeneous medium may generate beam aberrations and refractions that distort the focus and reduce its intensity, thereby affecting treatment efficiency.

One approach to ameliorating these problems involves focusing the transducer in water at a focal point and using a hydrophone to locate the focal point of maximum intensity. Each transducer element is separately activated at the maximum intensity point, and the phase of each signal is measured by the hydrophone. The measured phase for each element is compared to the expected phase to determine the phase deviation resulting from the geometric imperfections of the transducer elements and/or aberrations resulting from the water; the drive signal is then adjusted to compensate for the observed phase deviation. This approach, however, has a number of shortcomings. For example, because the hydrophone must be placed precisely at the focal point, this point must be identified with precision using, e.g., a highly accurate scanner and electronics; this setup may be expensive. In addition, the transducer elements are tested and calibrated sequentially, which is time consuming. Further, high ultrasonic intensities can damage or even destroy the hydrophone.

Another approach for calibrating the transducer geometric errors and/or beam aberrations resulting from the intervening medium involves placing a point source reflector (e.g., a microbubble) at the focal point. Reflected signals from the point source may be detected and the deviation between the measured phase of the reflected signal and the expected phase (based on the intended focal point) can be determined; the drive signal can then be adjusted to compensate for the deviation. But again, this approach requires an expensive scanner and electronics to identify the focal point so as to align the point source reflector therewith. In addition, at a high acoustic intensity, the point source reflector may produce microbubble cavitation and/or other non-linear effects on the target tissue, which may be difficult to control and which can interfere with the calibration procedure.

Accordingly, there is a need for efficient, economic and reliable approaches to compensating for deviations in the transducer geometry and inhomogeneities in an intervening medium as the ultrasound passes therethrough, thereby creating a high-quality focus.

SUMMARY

The present invention provides systems and methods for accurate and reliable calibration of transducer geometry as well as correction of beam aberrations caused by the inhomogeneous medium located between the transducer and the target region. In various embodiments, an acoustic reflector spanning a defined two-dimensional (2D) or three-dimensional (3D) area is placed on the beam path of ultrasound waves transmitted from one or more transducer elements to a focal zone. The acoustic reflector may be as simple as a mirror, and may or may not coincide with the focal zone. To calibrate the transducer geometry, the transducer elements may be energized to direct ultrasound beams to the acoustic reflector, and ultrasound reflections therefrom may be analyzed to determine the amplitudes and/or phases associated with the reflected ultrasound. The measured amplitudes and/or phases for the transducer element may then be compared to the expected amplitudes and/or phases to determine deviations therebetween. Subsequently, the drive signals of the transducer elements may be adjusted to compensate for the geometric imperfections. In addition, a "time of flight" associated with the reflections that defines a time interval from the time when the waves are transmitted from the transducer elements to the time when the waves are detected may be computed. Based on the time of flight, the actual location of each transducer element can be determined.

In addition, the location and/or orientation of the acoustic reflector may be adjusted during the calibration procedure; the transducer elements may then transmit a subsequent series of sonications to the reflector at the new location or having the new orientation, and receive reflections therefrom. In this way, multiple reflection measurements from distinct geometric locations may be obtained to accurately estimate the geometric information (e.g., absolute location) of the transducer elements. Alternatively or additionally, multiple acoustic reflectors may be utilized, and the transducer may transmit sonications to the acoustic reflectors. Based on the received reflections, the absolute locations of the transducer elements can be determined. As used herein, the term "absolute locations" refers to the coordinates of the transducer elements in the ultrasound coordinate system, or in some embodiments, in the environment (e.g., an MRI apparatus) in which they are implemented.

In some embodiments, optimal geometries of the transducer elements (as opposed to the actual absolute geometries of the transducer elements) are determined based on the reflection measurements. For example, the locational deviation of the transducer element from its expected location may be a small integer (e.g., less than 10) multiple of the ultrasound wavelength; in this situation, constructive interference may still occur at the focal zone. Therefore, the geometries of the transducer elements are considered "optimal" and there is no need for adjustment or compensation for the deviation. In other embodiments, a constant phase deviation occurs in all transducer elements 104 (this may be due to, for example, inaccurate prediction of the speed of ultrasound waves traversing the medium located between the transducer and acoustic reflector). In this situation, the ultrasound waves may still generate constructive interference at the focal zone; thus, the geometries of the transducer elements are also considered optimal and no adjustment/ compensation for the deviation is necessary.

In various embodiments, the acoustic reflector is configured to span a sufficiently large 2D or 3D area that allows ultrasound waves from all (or at least some) transducer elements travelling to the focal zone to be reflected. Thus, multiple transducer elements may be calibrated at once; this significantly reduces the calibration time required in conventional approaches. In addition, because the acoustic reflector is not required to coincide with the focal zone, ultrasound waves may be reflected by the reflector prior to reaching the focal zone, where the beam is most intense; thus, damage to the reflector resulting from a high acoustic intensity at the focal zone can be avoided. Further, because the acoustic reflector is not required to be aligned with the focal zone, the cost of implementing a scanning and aligning system in prior approaches is avoided.

To compensate for beam aberrations caused by the inhomogeneous medium located between the transducer and the target region, in various embodiments, the transducer elements are configured to generate the focal zone at or near the target region, and the acoustic reflector is, again, provided on the beam paths of ultrasound waves transmitted from the transducer elements to the target region (preferably near the target region). The acoustic reflector may be a cloud of microbubbles generated by the ultrasound waves and/or introduced parenterally by an administration system. In such implementations, the surface of the microbubble cloud forms an ultrasound reflector that reflects ultrasound waves before they reach the target region. By analyzing the reflections, the beam aberrations resulting from the inhomogeneous medium located between the transducer and the microbubble cloud may be determined. The transducer parameters (e.g., phase shifts and/or amplitudes) may then be adjusted in order to compensate for the aberrations.

In various embodiments, the location, configuration (e.g., shape) and/or size of the microbubble cloud are optimized to provide information about the beam aberrations while avoiding cavitation or other non-linear behavior of the microbubbles. In one implementation, the optimization is based on, for example, the locations and/or orientations of the transducer elements, the location and/or orientation of the target region, and/or characteristics of the target tissue and intervening medium.

Accordingly, in one aspect, the invention pertains to a method of calibrating the geometry of an ultrasound transducer having multiple transducer elements. In various embodiments, the method includes providing the first acoustic reflector spanning an area traversed by multiple beam paths of ultrasound waves transmitted from at least some of the transducer elements to a focal zone; causing some of the transducer elements to transmit the ultrasound waves to the focal zone; measuring reflections of the ultrasound waves off the first acoustic reflector; and based at least in part on the measured reflections, determining optimal geometric parameters (e.g., locations or orientations) associated with the transducer elements. The first acoustic reflector and the ultrasound transducer may have complementary contoured shapes or non-complementary contoured shapes. In some embodiments, the ultrasound transducer and the first acoustic reflector have concentric spherical shapes. In addition, the method may include analyzing the measured reflections to obtain a phase shift associated therewith and computing a phase difference between the phase shift and an estimated phase value; the optimal geometric parameters are then determined based at least in part on the computed phase difference. In one implementation, the method further includes estimating the speed of the ultrasound waves traversing a medium located between the transducer elements and the first acoustic reflector; the estimated phase value is determined based at least in part on the speed of the ultrasound waves.

The method may include computing a time of flight of the ultrasound waves from the time when the ultrasound waves are transmitted from the transducer elements to the time when the reflections are measured. In addition, the method may include estimating the speed of the ultrasound waves traversing the medium located between the transducer elements and the first acoustic reflector; the actual geometric parameters may then be determined based on the time of flight and the estimated speed of the ultrasound waves. Further, the method may include adjusting parameter values associated with the transducer elements based at least in part on the measured reflections so as to improve a focus in the focal zone. The parameter values may include frequencies, phases, and/or amplitudes of signals driving the transducer elements.

The reflections of the ultrasound waves may be measured by the transducer elements and/or an acoustic-signal detection device. In various embodiments, the method includes moving the first acoustic reflector from the first location to the second location, different from the first location; measuring reflections of the ultrasound waves off the first acoustic reflector at the second location; and based at least in part on the measured reflections from the first and second locations, determining absolute geometric parameters associated with the transducer elements. In other embodiments, the method includes providing the second acoustic reflector at the second location; causing some of the transducer elements to transmit the ultrasound waves to the focal zone; measuring reflections of the ultrasound waves off the first and second acoustic reflectors; and based at least in part on the measured reflections, determining absolute geometric parameters associated with the transducer elements. The method may further include modulating the ultrasound frequency of the transmitted waves and determining the geometric parameters associated with the transducer elements based at least in part on the reflections off the first acoustic reflector. In one implementation, the ultrasound frequency is modulating by multiple lower frequencies. Alternatively, the method may include causing the transducer elements to sequentially transmit multiple series of the ultrasound waves, each series corresponding to a different frequency, and determining the geometric parameters associated with the transducer elements based at least in part on the reflections off the first acoustic reflector.

In another aspect, the invention relates to a system for calibrating the geometry of an ultrasound system. In various embodiments, the system includes an ultrasound transducer having multiple transducer elements; the first acoustic reflector spanning an area traversed by multiple beam paths of ultrasound waves transmitted from at least some of the transducer elements to a focal zone; and a controller configured to: cause some of the transducer elements to transmit the ultrasound waves to the focal zone; cause measurements to be made of reflections of the ultrasound waves off the first acoustic reflector; and based at least in part on the reflection measurements, determine optimal geometric parameters (locations or orientations) associated with the transducer elements. The first acoustic reflector and the ultrasound transducer may have complementary contoured shapes or non-complementary contoured shapes. In some embodiments, the ultrasound transducer and the first acoustic reflector have concentric spherical shapes. In addition, the controller may be further configured to analyze the measured reflections to obtain a phase shift associated therewith and compute a phase difference between the phase shift and an estimated phase value; the optimal geometric parameters may then be determined based at least in part on the computed phase difference. In one implementation, the controller is further configured to estimate the speed of the ultrasound waves traversing a medium located between the transducer elements and the first acoustic reflector; the estimated phase value is determined based at least in part on the speed of the ultrasound waves.

In various embodiments, the controller is further configured to compute a time of flight of the ultrasound waves from the time when the ultrasound waves are transmitted from the transducer elements to the time when the reflections are measured. In addition, the controller is further configured to estimate the speed of the ultrasound waves traversing the medium located between the transducer elements and the first acoustic reflector; wherein the actual geometric parameters are then determined based on the time of flight and the estimated speed of the ultrasound waves. Further, the controller may be configured to adjust parameter values associated with the transducer elements based at least in part on the measured reflections so as to improve a focus in the focal zone. The parameter values may include frequencies, phases, and/or amplitudes of signals driving the transducer elements.

The reflections of the ultrasound waves may be measured by the transducer elements. Alternatively, the system may include an acoustic-signal detection device to measure the reflections of the ultrasound waves. In some embodiments, the system further includes an adjustment mechanism for adjusting the orientation and/or location of the first acoustic reflector. The controller is then configured to cause the adjustment mechanism to move the first acoustic reflector from the first location to the second location, different from the first location; measure reflections of the ultrasound waves off the first acoustic reflector at the second location; and based at least in part on the measured reflections from the first and second locations, determine absolute geometric parameters associated with the transducer elements. In other embodiments, the system further includes the second acoustic reflector located at the second location, different from the first location. The controller is further configured to cause some of the transducer elements to transmit the ultrasound waves to the focal zone; measure reflections of the ultrasound waves off the first and second acoustic reflectors; and based at least in part on the measured reflections, determine absolute geometric parameters associated with the transducer elements. The controller may be further configured to modulate the ultrasound frequency of the transmitted waves and determine the geometric parameters associated with the transducer elements based at least in part on the reflections off the first acoustic reflector. In one implementation, the controller is further configured to modulate the ultrasound frequency by multiple lower frequencies. Alternatively, the controller may be further configured to cause the transducer elements to sequentially transmit multiple series of the ultrasound waves, each series corresponding to a different frequency, and determine the geometric parameters associated with the transducer elements based at least in part on the reflections off the first acoustic reflector.

Another aspect of the invention relates to a system for focusing an ultrasound transducer having multiple transducer elements on a target region. In various embodiments, the system includes an acoustic reflector configured to span an area in an intervening medium through which ultrasound waves from the transducer travel; and a controller configured to cause at least some transducer elements to transmit the ultrasound waves to the target region; cause measurements to be made of reflections of the ultrasound waves off the acoustic reflector; and based at least in part on the reflection measurements, adjust parameter values associated with the transducer elements so as to compensate for beam aberrations resulting from the intervening medium. The parameter values may include frequencies, phases, and/or amplitudes of signals driving the transducer elements. In one implementation, the area spanned by the acoustic reflector is traversed by multiple beam paths of ultrasound waves transmitted from at least some of the transducer elements to the target region.

In addition, the system may include an administration device for an exogenous agent; microbubbles in the exogenous agent may form the acoustic reflector. In various embodiments, the administration device includes an introducing device (e.g., a needle and/or a catheter.) for delivering the exogenous agent into the intervening medium and an actuation mechanism (e.g., a syringe and/or a peristaltic pump) for dispensing the exogenous agent from the introducing device; the controller is further configured to control activation and deactivation of the actuation mechanism. Additionally or alternatively, the controller may be further configured to cause the transducer elements to transmit ultrasound waves so as to generate microbubbles that form the acoustic reflector. In addition, the reflections of the ultrasound waves may be measured by the transducer elements. Alternatively, the system may include an acoustic-signal detection device to measure the reflections of the ultrasound waves. The acoustic reflector and the ultrasound transducer may have complementary contoured shapes, concentric spherical shapes, or different contoured shapes.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
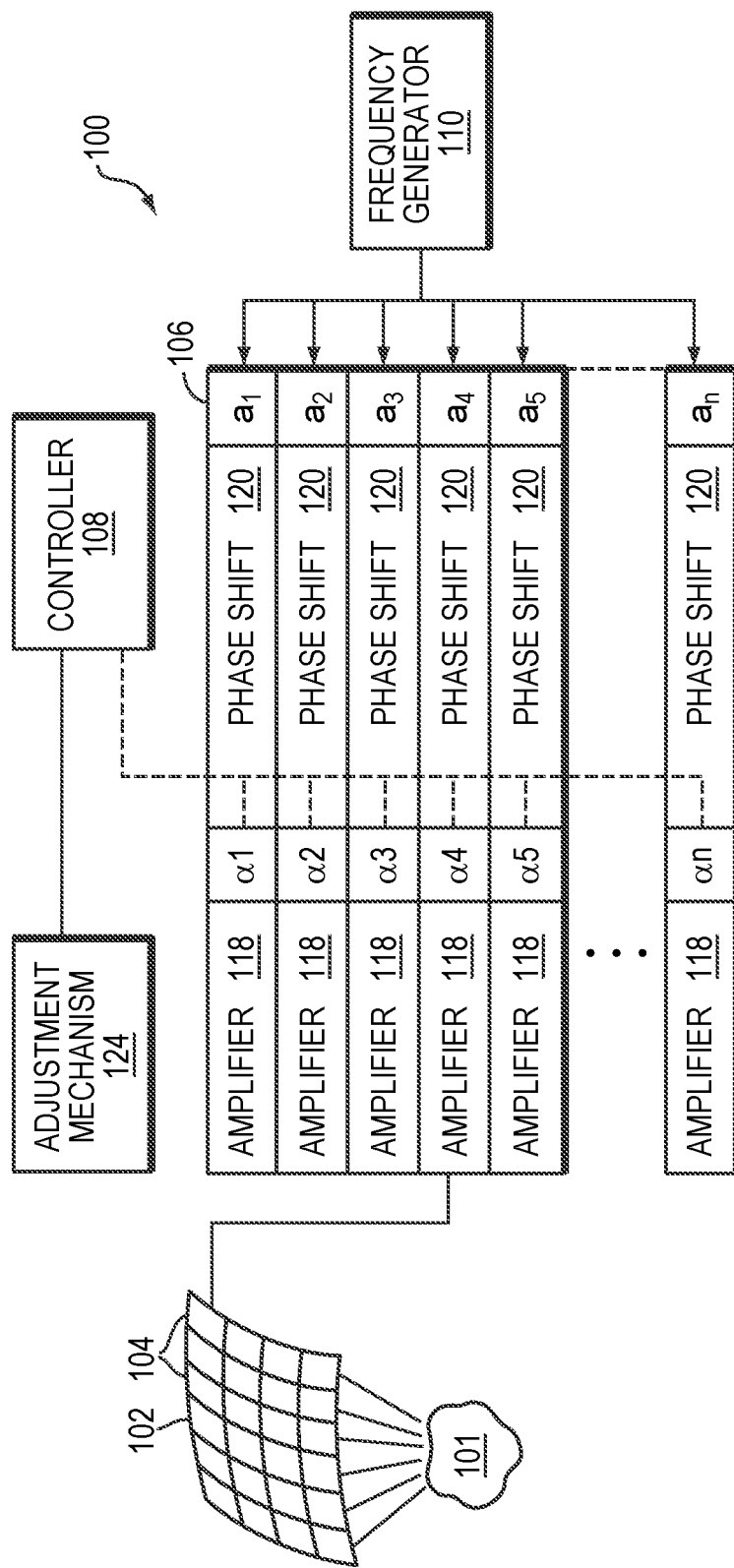
FIG. 1 illustrates a focused ultrasound system in accordance with various embodiments.

FIG. 1 illustrates an exemplary ultrasound system 100 for generating and delivering a focused acoustic energy beam to a target region 101 within a patient's body. The illustrated system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) or other contoured shape suitable for placement on the surface of the patient's body, or may include one or more planar or otherwise shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radio frequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the intervening medium (e.g., a fluid and/or tissue) located between the transducer elements 104 and the target region onto the target region 101, and account for wave distortions induced in the intervening medium. The amplification factors and phase shifts are computed using the controller 108, which may provide the computational functions through software, hardware, firmware, hardwiring, or any combination thereof. In various embodiments, the controller 108 utilizes a general-purpose or special-purpose digital data processor programmed with software in a conventional manner, and without undue experimentation, to determine the frequency, phase shifts and/or amplification factors of the transducer elements 104. In some embodiments, the system 100 may further include an adjustment mechanism 124 (e.g., a motor, a gimbal, or other manipulator) that permits orientation and/or location adjustment of an acoustic reflector as further described below.

Figure 2:
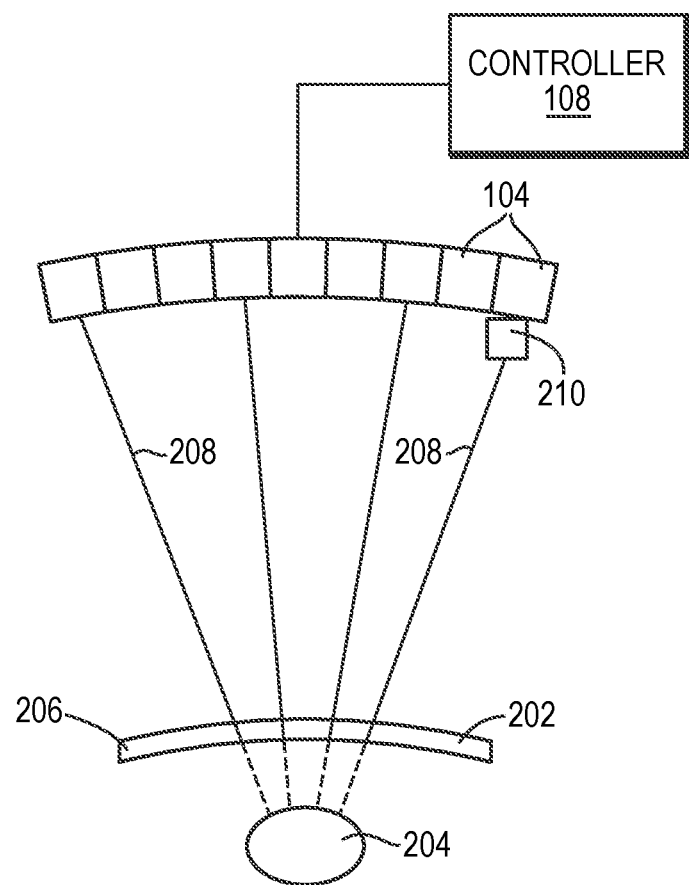
FIG. 2 depicts an acoustic reflector employed for performing a transducer calibration procedure in accordance with some embodiments.

To create a high-quality focus, it may be necessary to calibrate the transducer 102 and take into account transducer geometric imperfections resulting from, for example, movement, shifts and/or deformation of the transducer elements 104 from their expected locations. Referring to FIG. 2, in some embodiments, the calibration procedure involves implementation of an acoustic reflector 202 located between the transducer 102 and a focal zone 204 generated by the ultrasound waves. In various embodiments, the acoustic reflector 202 is configured to span a defined 2D or 3D area 206 that intersects with beam paths 208 of the ultrasound waves transmitted from all (or at least some) transducer elements 104 to the focal zone 204. Thus, the ultrasound waves transmitted from all (or at least some) transducer elements 104 may be reflected by the reflector 202 at once. In some embodiments, the reflected waves are detected by the transducer elements 104 and/or an acoustic-signal detection device 210, and subsequently provided to the controller 108 for further processing as further described below.

Figure 3A:
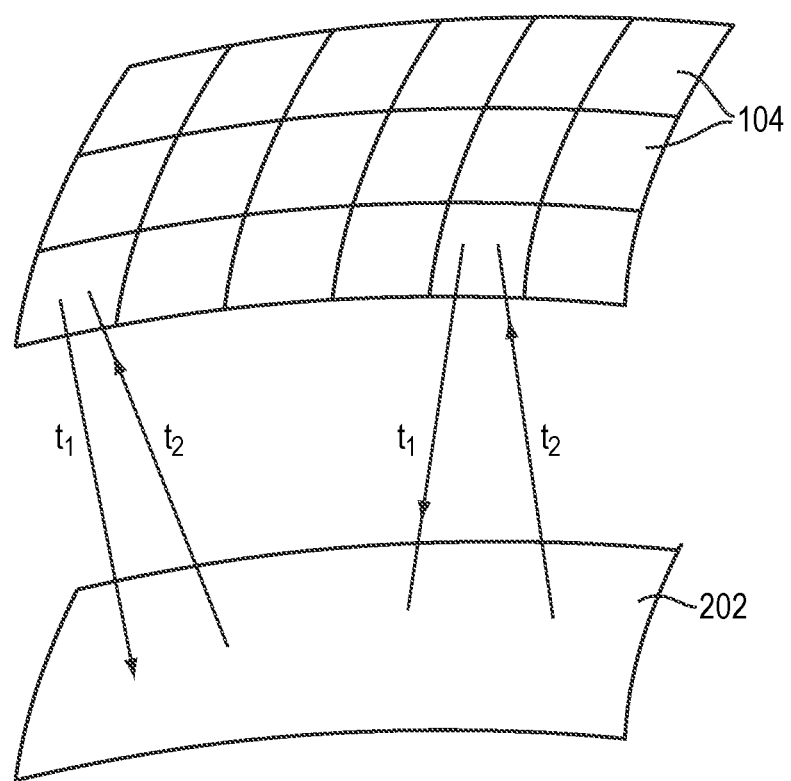
FIGS. 3A and 3B depict various configurations of the transducer elements performing a transducer calibration procedure in accordance with various embodiments.
Figure 3B:
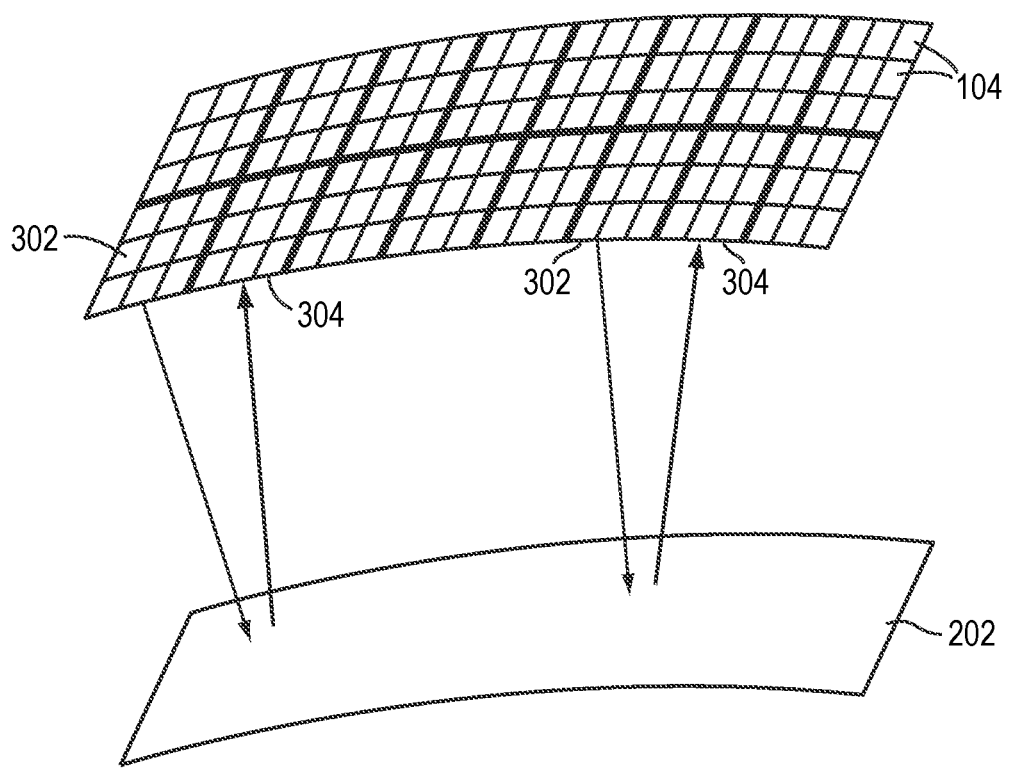

The acoustic-signal detection device 210 may be integrated with the ultrasound system 100 or, alternatively, may form a stand-alone device in communication with the ultrasound system 100. In one embodiment, the transducer elements 104 possess both transmit and detect capabilities. Referring to FIG. 3A, in one embodiment, each individual transducer element 104 alternates between transmitting ultrasound signals to the acoustic reflector 202 and receiving ultrasound signals reflected therefrom. For example, all transducer elements 104 may substantially simultaneously transmit ultrasound to the acoustic reflector 202 at a time $t_1$ and subsequently receive echo signals therefrom at a time $t_2$. Referring to FIG. 3B, in one implementation, the transducer array 102 is divided into a transmit region 302 and a receive region 304; transducer elements in the transmit region 302 transmit the ultrasound waves while transducer elements in the receive region 304 receive the reflected waves. The received reflected waves are then transmitted to the controller 108 for analysis. The transmit region 302 and receive region 304 may be configured in different patterns and shapes at various locations of the transducer array.

Figure 4A:
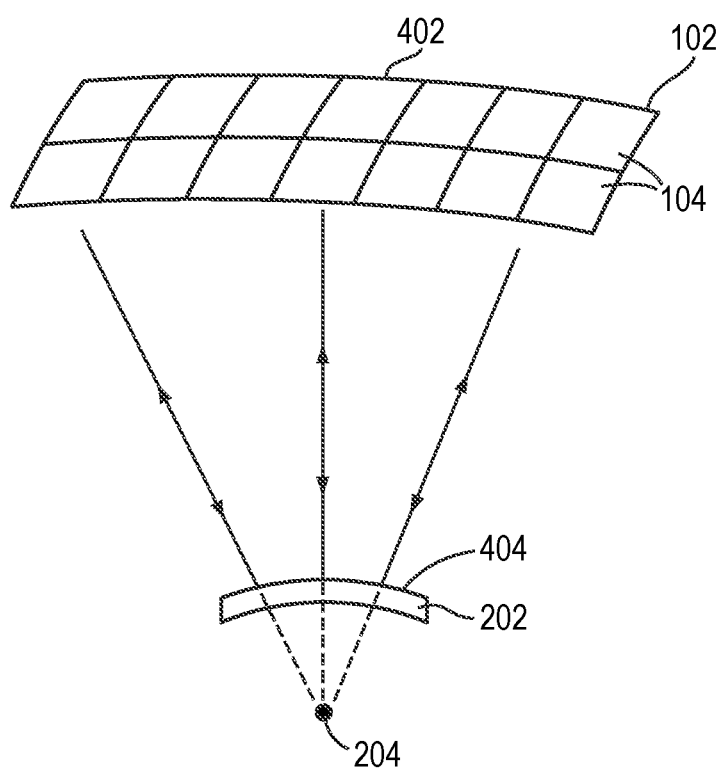
FIGS. 4A and 4B depict various configurations of an acoustic reflector in accordance with various embodiments.

In addition, the acoustic reflector 202 may be configured to have the same or similar curved shape as the transducer array 102. For example, referring to FIG. 4A, the transducer array 102 may have a spherical shape 402 with a center at the focal zone 204. In various embodiments, the acoustic reflector 202 is configured to have a spherical shape 404 concentric with the spherical shape 402 of the transducer array 102. Accordingly, ultrasound waves transmitted from the elements 104 to the center (i.e., the focal zone 204) may be reflected by the reflector 202 and received by the same elements 104 that transmit the waves.

Figure 4B:
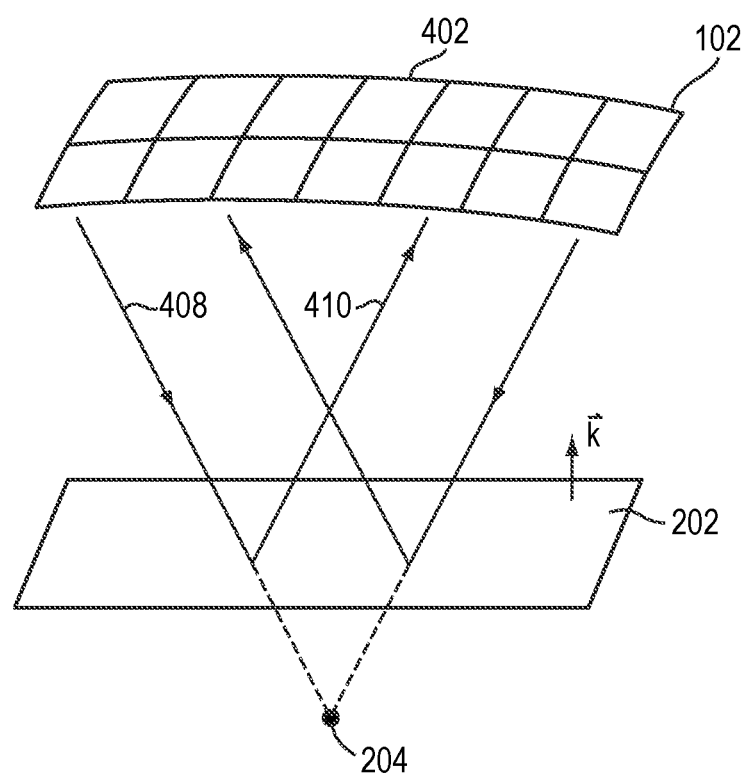

Alternatively, the shape of the acoustic reflector 202 may be different from that of the transducer array. For example, referring to FIG. 4B, while the transducer array 102 has a spherical shape, the illustrated acoustic reflector 202 has a flat planar shape. In this configuration, the reflected waves may be detected by the transducer elements 104 different from those transmitting the waves. Regardless of the shape of the reflector 202, the transducer elements 104 and/or the detection device 210 may be activated to detect the reflected waves from the reflector 202 based on the geometric arrangements of the acoustic reflector 202 and the elements 104 that transmit the waves. For example, based on the direction of a beam path 408 and the orientation $\vec{k}$ of the reflector 202, the angle of reflection of the reflected waves can be computed. The transducer element located on the beam path 410 of the reflected waves may then be activated to detect the reflected waves. In various embodiments, the transmitting and receiving transducer elements are synchronized so as to ensure accurate timing and measurements.

In one embodiment, multiple acoustic reflectors may be utilized, and the transducer may transmit sonications to the acoustic reflectors. Based on the received reflections, the absolute locations of the transducer elements can be determined. As used herein, the absolute locations refer to the coordinates of the transducer elements in the ultrasound coordinate system, or in some embodiments, in the environment (e.g., an MRI apparatus) in which they are implemented.

Additionally or alternatively, the absolute locations of the transducer elements 104 may be determined using a frequency-modulation approach. For example, the ultrasound frequency of the waves transmitted from the transducer elements 104 may be modulated with multiple lower frequencies; the phase shifts of the signals reflected from the acoustic reflector 202 may be analyzed to determine the absolute locations of the transducer elements. In one embodiment, the beamformer 106 causes the transducer elements 104 to transmit two modulating frequencies, $f_1$ and $f_2$ (e.g., 1 kHz and 100 Hz), and the ultrasound frequency, $f_3$ (e.g., 25 kHz), with no phase shifts with respect to each other to the acoustic reflector 202. The phase shift $\varphi_1$ of the received waves at the modulating frequency of 100 Hz (which has the longest wavelength $\lambda_1$ among the three frequencies) is first analyzed to estimate the distance, d, between the transducer elements and the reflector 202, given by:

$$d = d_1 = \frac{\varphi_1}{2\pi}\lambda_1$$

The phase shift $\varphi_2$ of the received waves at the modulating frequency of 1 kHz (having a shorter wavelength $\lambda_2$) can then be analyzed to provide a finer resolution of the estimation. This is because for the same change in the phase shifts, the higher frequency has a shorter corresponding distance. For example, a phase shift of $\pi$ corresponds to the distances of 1.7 m and 170 mm for the 100 Hz and 1 kHz signals, respectively. Thus, a more accurate approximation to the measured range, $d_2$, can be obtained from:

$$d_2 = \frac{\varphi_2}{2\pi}\lambda_2$$

and the distance, d, is estimated by:

$$d = \text{Int}\left[\frac{d_1}{\lambda_2}\right] \times \lambda_2 + \frac{\varphi_2}{2\pi}\lambda_2$$

Similarly, the measured range $d_3$ corresponding to the phase shift $\varphi_3$ at the frequency of 25 kHz is given by:

$$d_3 = \frac{\varphi_3}{2\pi}\lambda_3$$

and the distance, d, is estimated by:

$$d = \text{Int}\left[\frac{d_2}{\lambda_3}\right] \times \lambda_3 + \frac{\varphi_3}{2\pi}\lambda_3$$

As a result, the distance, d, between the transducer elements and the reflector 202 can be computed by:

$$d = \text{Int}\left[\frac{\varphi_1(t)}{2\pi} \times \frac{f_2}{f_1}\right] \times \frac{c}{f_2} + \text{Int}\left[\frac{\varphi_2(t)}{2\pi} \times \frac{f_3}{f_2}\right] \times \frac{c}{f_3} + \frac{\varphi_3(t)}{2\pi} \times \frac{c}{f_3}. \quad \text{Eq. (1)}$$

where c represents the speed of ultrasound waves traversing the medium located between the transducer 102 and the acoustic reflector 202. Accordingly, by modulating the ultrasound frequency with lower frequencies, the absolute locations of the transducer elements 104 may be determined using the equation above. In some embodiments, instead of frequency modulation, multiple frequencies (e.g., $f_1$ $f_2$, and $f_3$) are sequentially applied to the focal zone; reflections from the acoustic reflector 202 may be analyzed to determine the absolution locations of the transducer elements 104 using Eq. (1).

The location and/or orientation of the acoustic reflector 202 may be adjusted during the calibration procedure; the transducer elements 104 may then transmit a subsequent series of sonications to the reflector 202 at the new location or having the new orientation, and receive reflections therefrom. In this way, multiple reflection measurements from distinct geometric locations may be obtained to accurately estimate the geometric information of the transducer elements 104. It should be noted that in this approach, the exact location of the acoustic reflector 202 is not critical so long as that the reflector 202 intersects with beam paths 208 of the ultrasound waves and reflects the ultrasound waves; the controller 108 may analyze the measured reflections and the relative geometric arrangements of the acoustic reflector 202 and the elements 104 to obtain information (e.g., the amplitudes and/or phases) associated with the transducer elements 104 as further described below. Adjustment of the location/orientation of the acoustic reflector 202 may be performed manually by a user or automatically by the adjustment mechanism 124. For example, the adjustment mechanism 124 may physically rotate the acoustic reflector 202 around one or more axes thereof and/or move the acoustic reflector 202 with respect to the transducer 102 to a desired location. In some embodiments, the adjustment mechanism 124 is responsive to a communication from the controller 108. Thus, the controller 108 may, based on the detected reflections from the acoustic reflector 202 at the current location with the current orientation, determine the new orientation/location of the acoustic reflector 202 (if an adjustment is desired), and cause the adjustment mechanism 124 to move the acoustic reflector 202 accordingly.

The detected reflections may be provided to the controller 108 to obtain information, such as the amplitudes and/or phases, associated therewith. In one embodiment, the controller 108 compares the phases of the measured reflections, $\varphi_{measure}$, to the expected phases of the reflections, $\varphi_{expect}$, that are determined based on the expected geometry of the transducer elements, and computes the difference therebetween ($\Delta\varphi = \varphi_{measure} - \varphi_{expect}$). The controller 108 may then operate the transducer elements 104 in accordance with the difference to compensate for the output errors resulting from geometric imperfections. In some embodiments, the controller 108 further computes the "time of flight" of the ultrasound waves between their emission by the transducer elements to when the reflected waves are received by the same or different transducer elements or by the acoustic-signal detection device 210. In addition, the controller may estimate the speed of ultrasound waves traversing the medium located between the transducer 102 and the acoustic reflector 202 based on an acoustic ray model, a pre-clinical study, a pre-treatment procedure, and/or from known literature. Systems and methods for estimating the speed of ultrasound waves traversing the medium are described, for example, in U.S. patent application Ser. No. 15/613,940, the entire disclosure of which is hereby incorporated by reference. Based on the measured time of flight and the estimated speed of sound in the medium, the location of each transducer element may be determined. Again, the controller 108 may compare the measured locations to the expected locations of the elements, determine deviations therebetween and operate the elements to compensate for the deviations.

Accordingly, by using the acoustic reflector 202, the actual locations and orientations of the transducer elements can be determined, and the drive signals thereof can be adjusted to compensate for the geometric differences between the actual and expected locations and orientations. In addition, because the acoustic reflector 202 spans an area traversed by multiple beam paths 208 of the ultrasound waves from the transducer elements 104, multiple transducer elements may be calibrated substantially simultaneously. In one embodiment, the acoustic reflector 202 spans a sufficiently large area to allow all transducer elements to be calibrated using the above-described approach substantially simultaneously. This advantageously obviates the need for sequentially moving a hydrophone or a point-source reflector into alignment with each of the elements as in prior approaches, and thereby significantly decreases the calibration time and eliminates the cost of the aligning/scanning system. Further, because the acoustic reflector 202 is placed on the beam paths between the transducer 102 and the focal zone 204, the ultrasound waves are reflected therefrom prior to reaching the focal zone; therefore, only a limited acoustic intensity is generated at the acoustic reflector 202. This approach avoids the possibility of damage to the hydrophone or point-source reflector as in prior approaches. Finally, because the acoustic reflector 202 may be a simple metal sheet or a highly reflective material coated on a suitable substrate, it may be economical to implement the ultrasound calibration procedure described herein.

Figure 5A:
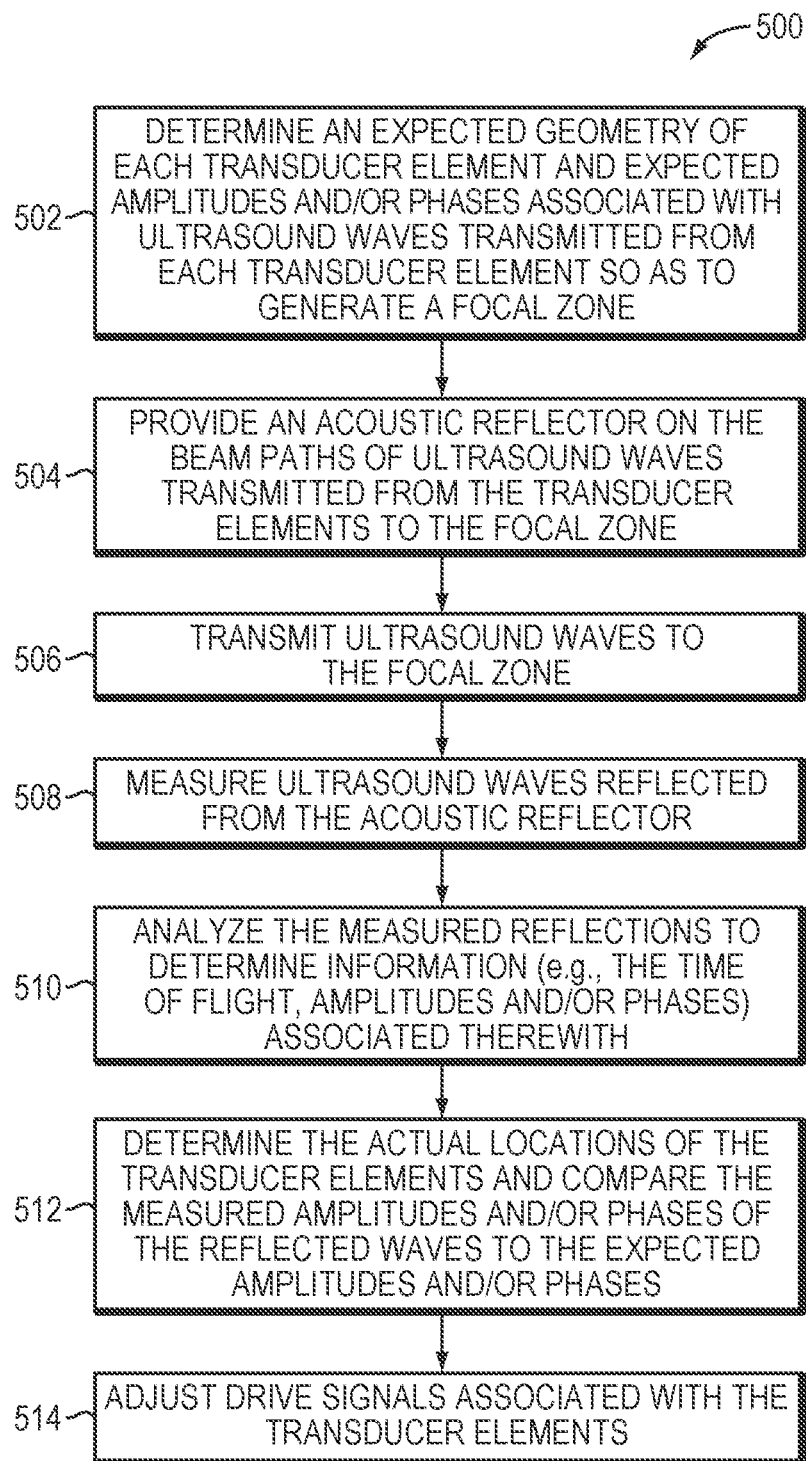
FIG. 5A is a flow chart illustrating an approach for calibrating geometries of transducer elements in accordance with various embodiments.

FIG. 5A is a flow chart illustrating an approach 500 for calibrating geometries of transducer elements in accordance with various embodiments. In a first step 502, a controller may determine or retrieve from memory the expected geometry (e.g., location and/or orientation) of each transducer element 104 in the ultrasound system 100 based on, for example, the manufacturing design. In addition, based on the expected geometry, the controller may determine the expected amplitudes and/or phases associated with ultrasound waves transmitted from each transducer element so as to generate a focal zone. In a second step 504, an acoustic reflector is provided on the beam paths of ultrasound waves transmitted from the elements 104 to the focal zone. The acoustic reflector may be configured to span an area intersecting with the beam paths of multiple (or all) transducer elements 104. In addition, the acoustic reflector may be optionally configured to have a similar contoured shape as that of the transducer 102. In a third step 506, the transducer elements transmit ultrasound waves to the focal zone located behind the acoustic reflector. In a fourth step 508, ultrasound reflected from the acoustic reflector is measured using the transducer and/or acoustic-signal detection device 210. In a fifth step 510, the controller 108 analyzes the measured reflections to determine information (e.g., the time of flight, amplitudes and/or phases) associated therewith. In a sixth step 512, based on the measured time of flight, the controller 108 may determine the actual locations of the transducer elements. In addition, the controller 108 may compare the measured amplitudes and/or phases of the reflected waves to the expected amplitudes and/or phases to determine differences therebetween. Subsequently, in a seventh step 514, the controller 108 may cause the beamformer 106 to adjust drive signals associated with the transducer elements based on the determined differences in locations, amplitudes and/or phases so as to compensate for the output errors resulting from geometric anomalies of the transducer elements 104.

The above-described approach is particularly suitable for correcting geometries of transducer elements that have locational deviations of less than a half wavelength from their expected positions (i.e., the resulting phase shifts are less than π). If the phase shifts associated with the geometric imperfections exceeds π, phase wrapping may occur. Because the beam path transmitted from each element 104 to the focal zone 204 is substantially perpendicular to the emitting surface of the element 104 and the goal of the ultrasound procedure is to create a constructive interference of the beams at the focal zone 204, in various embodiments, no phase correction is necessary if the locational deviation, d, of the element from its expected position satisfies a condition: d=n×wavelength, where n is a small integer (e.g., less than 10).

In addition, a constant phase shift may occur in all elements 104. This may result from, for example, an inaccurate prediction of the speed of ultrasound waves traversing the ultrasound medium (e.g., water) located between the transducer elements 104 and the acoustic reflector 202; inaccurate prediction of the speed of the ultrasound waves may cause inaccurate predictions of the phase shifts associated with the ultrasound waves when traversing the medium. Therefore, the measured phase shifts may all have a constant deviation from the expected values across all transducer elements. But, again, because the goal of the ultrasound procedure is to create constructive interference at the focal zone, it may not be necessary to correct the constant phase shift occurring in all elements.

Accordingly, in some embodiments, even if measurements of the reflection waves indicate deviations between the measured amplitudes and/or phases of the reflected waves and the expected amplitudes and/or phases, the controller 108 may determine that compensations for the differences are unnecessary (e.g., when the deviation of the element location from its expected location is an integer multiple of the wavelength of the ultrasound waves and/or when a constant phase shift occurs in all elements 104). Therefore, referring to FIG. 5B, utilizing this approach, the absolute geometries of the transducer elements are not critical; rather, the controller 108 determines an optimal configuration and optimal parameters (e.g., amplitudes and/or phases) associated with the transducer elements 104 for achieving target focal properties at the focal zone 204 (step 516). During the ultrasound procedure, the transducer elements 104 may be driven based on the determined optimal parameters (step 518).

As set forth above, variations in the phase shifts may occur when the speed of ultrasound waves traversing the medium located between the transducer and the acoustic reflector changes. Therefore, it is critical to ensure that the change in the speed of ultrasound waves in the medium is insignificant (e.g., within 10% or, in some embodiments, 5%). As the temperature of the medium directly affects the speed of sound therein, in some embodiments, the temperature of the medium is monitored using, for example, an MRI apparatus. If a significant change is detected, the prediction of the speed of ultrasound waves (and thereby the phase shifts) may be adjusted; consequently, the phase deviations between the measured phase shifts and predicted phase shifts may be recomputed.

Figure 6:
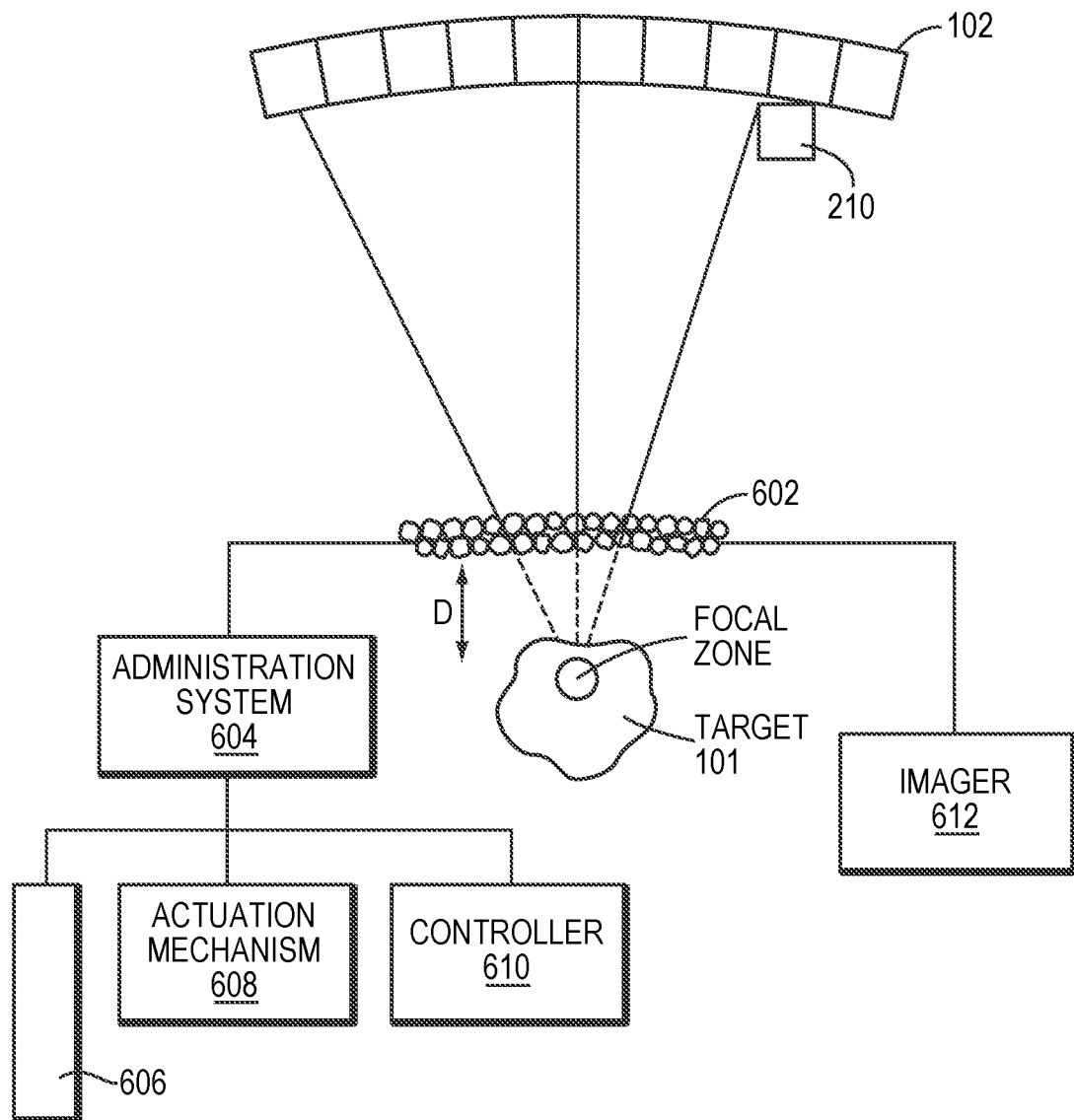
FIG. 6 depicts an acoustic reflector employed for measuring aberrations of ultrasound waves when travelling through a medium in accordance with some embodiments.

In various embodiments, the acoustic reflector 202 is configured to facilitate determination of beam aberrations caused by the inhomogeneous medium located between the transducer 102 and the target region 101. For example, referring to FIG. 6, the transducer elements 104 may be configured to generate a focal zone at or near the target region 101, and an acoustic reflector 602 may, again, be provided on the beam paths of ultrasound waves from the transducer array 102 to the target region 101. In one implementation, the acoustic reflector is a cloud of microbubbles generated by the ultrasound waves and/or introduced by an administration system 604; the surface of the microbubble cloud 602 collectively forms the reflector reflecting the ultrasound waves prior to reaching the target region 101. In addition, the microbubble cloud 602 may be configured to occupy a sufficiently large area such that the ultrasound beams from more than one transducer element 104 can be reflected therefrom. The ultrasound waves reflected from the microbubble cloud 602 may be detected by the acoustic-signal detection device 210 and/or transducer elements 104 as described above and subsequently provided to the controller 108 for further processing. The administration system 604 may be as simple as a catheter or a needle. In some embodiments, the administration system 604 includes a more complex system for controllably introducing an exogenous agent (e.g., an ultrasound contrast agent or any other suitable agent) carrying the microbubbles. For example, the administration system 604 may include an introducing device (e.g., a catheter or a needle) 606 for delivering the exogenous agent into the patient's body; an actuation mechanism (e.g., a syringe, a peristaltic pump, etc.) 608 for forcing the exogenous agent to be dispensed from the introducing device 606, and a controller 610 for controlling activation and deactivation of the actuation mechanism so as to control the delivery dose, timing and/or profile of the exogenous agent (and thereby the microbubbles). The controller 610 and the ultrasound controller 108 may be implemented in a single, integrated control facility or form two stand-alone devices in communication therebetween. Examples of suitable administration systems are described in the U.S. Patent Application entitled "Controlling Delivery of Therapeutic Agent in Microbubble-Enhanced Ultrasound Procedures" filed on even date herewith, the contents of which are incorporated herein by reference.

In various embodiments, the controller 108 analyzes the reflections to obtain information, such as the amplitudes and/or phases, associated with the reflected beams. In one embodiment, the controller 108 compares the phases of the measured reflections, $\varphi_{ref}$, to the phases of the transmitted waves, $\varphi_{tra}$, and determines the difference therebetween ($\Delta\varphi=\varphi_{ref}-\varphi_{tra}$). The difference results from the beam aberrations arising from the intervening medium. Based thereon, the controller 108 operates the transducer elements 104 to compensate for these aberrations during ultrasound treatment, thereby providing a high-quality focus at the target region.

In some embodiments, the controller 108 causes each transducer element 104 to transmit another ultrasound beam having a phase shift of the determined phase difference, $\Delta\varphi$, to the focal zone and measures the resulting reflections from the microbubble cloud 602. Again, the phase difference between the reflected and transmitted ultrasound may be set as the phase value correction for the next sonication. This process can be iteratively implemented until the phase difference between the reflected and transmitted waves is below a threshold value (e.g., 10°), which indicates successful compensation for the beam aberrations resulting from the medium located between the transducer 102 and microbubble cloud 602. Other conditions, however, may dictate when to phase adjustment can be considered complete. For example, phase adjustment may be stopped when too may iterations (e.g., more than 20) have been performed or when the improvement of the deviation between two successive iterations is too small (e.g., $\Delta\varphi_{n+1}-\Delta\varphi_n<5°$).

Figure 5B:
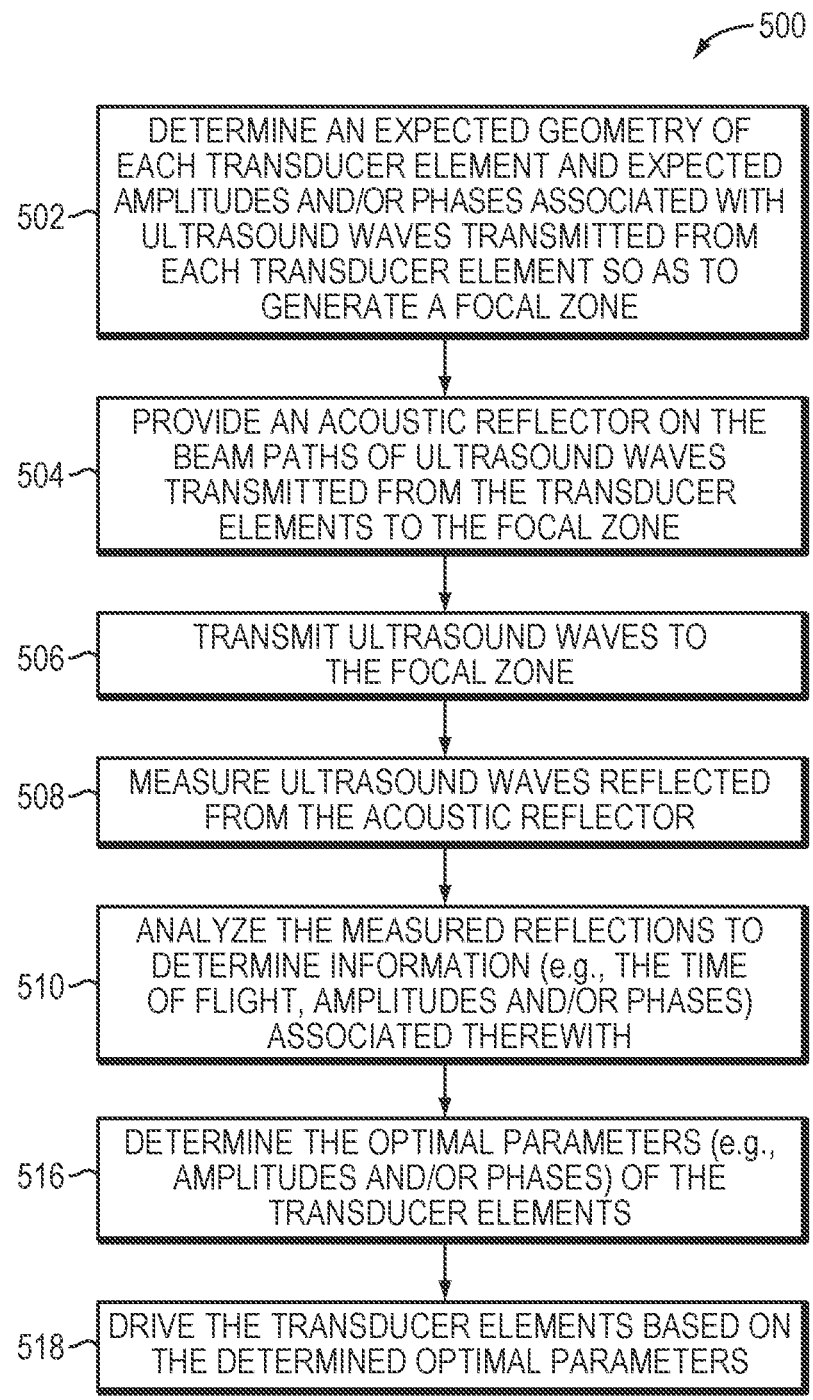
FIG. 5B is a flow chart illustrating an approach for achieving target focal properties at a focal zone in accordance with various embodiments.

In addition, similar to the acoustic reflector 202 implemented in FIG. 5B, the controller 108 may determine that compensation for the deviation of the measured phase shift from the expected phase shift is unnecessary. This typically occurs when, for example, the deviation of the measured location of the transducer element 104 from its expected location is a small integer (e.g., less than 10) multiple of the wavelength of the ultrasound waves and/or when a constant phase shift occurs in all transducer elements 104. Again, the absolute geometries of the transducer elements are not critical; rather, the controller 108 determines an optimal configuration of the transducer elements 104 and their associated parameters (e.g., amplitudes and/or phases) that can achieve target focal properties at the focal zone. Further, the administration system 604 may introduce the microbubble reflector 602 at various locations on the beam paths of ultrasound waves from the transducer array 102 to the target region 101 so as to provide multiple reflection measurements from distinct geometric locations for each transducer element 104; this may increase the estimation accuracy of the transducer geometries. Again, the exact location of the microbubble reflector 602 is not critical so long as that the reflector 602 intersects with beam paths of the ultrasound waves and reflects the ultrasound waves; the controller 108 can obtain information (e.g., the amplitudes and/or phases) associated with the transducer elements 104 based on the detected reflections and the relative geometric arrangements of the acoustic reflector 602 and the transducer elements 104.

Because the ultrasound focus is generated at the target region 101, by increasing the distance, D, between the locations of the microbubble cloud 602 and the target region 101, the acoustic intensity at the microbubble cloud 602 may be reduced to avoid cavitation events and/or other non-linear behavior of the microbubbles, thereby avoiding damage to the intervening tissue and potentially interfering with calibration. Although increasing the distance D may reduce microbubble cavitation, it comes with a trade-off—the beam aberrations caused by the medium located within this distance are not compensated for. In some embodiments, the controller 108 determines the optimal location of the microbubble cloud 602 based on information about the characteristics (e.g., structure, homogeneity, density, etc.) of the medium and their effects on propagation of acoustic beams. For example, if a large portion of the tissue surrounding the target region 101 is highly homogeneous and thereby causes limited beam aberrations, the distance D between the microbubble cloud 602 and the target region 101 may be increased to avoid microbubble cavitation. Conversely, if the tissue surrounding the target region 101 is highly inhomogeneous and has a high tolerance for heat, the distance D between the microbubble cloud 602 and the target region 101 may be reduced to increase the measurement accuracy of beam aberrations caused by inhomogeneity of the intervening tissue. In various embodiments, the optimal location, configuration (e.g., shape) and/or spanning area of the microbubble cloud 602 are determined based on, for example, the relative locations of the transducer elements 104 with respect to the target region 101 and/or the characteristics of the target tissue and/or the intervening medium as these factors bear on aberration of beams travelling though the medium, as well as the desire to avoid microbubble cavitation or other non-linear behavior.

In various embodiments, information about the characteristics of the intervening medium and/or target region 101 is obtained using an imager 612, such as a magnetic resonance imaging (MRI) device, a computer tomography (CT) device, a positron emission tomography (PET) device, a single-photon emission computed tomography (SPECT) device, or an ultrasonography device. The imager 612 may provide a set of 2D images suitable for reconstructing a 3D image of the intervening medium and/or target region; alternatively, image acquisition may be 3D. In addition, image-manipulation functionality may be implemented in the imager 612, in the controller 108, or in a separate device.

In addition, the location, configuration and/or spanning area of the microbubble cloud 602 may be manipulated using, for example, an acoustic radiation force created by the ultrasound waves. The acoustic radiation force is produced by a change in the density of energy and momentum of the propagating ultrasound waves resulting from absorption, scattering or reflection from the medium. Generally, the amplitude of the acoustic radiation force is proportional to the ultrasound intensity. Accordingly, in one implementation, the intensity of the ultrasound beams directed to the microbubble cloud 602 gradually increases until the generated acoustic radiation force suffices to manipulate and move the microbubbles in the cloud 602. In another embodiment, prior to manipulation of the microbubble cloud, the characteristics (e.g., the absorption coefficient) of the intervening medium are measured as described above; the ultrasound intensity sufficient to move microbubbles in the cloud 602 can be computed based thereon.

Alternatively, an ultrasound steering beam may be created to apply stress on the microbubbles in the cloud 602 so as to move them. The ultrasound steering beam may be generated mechanically or electrically. In one embodiment, the transducer elements 104 are physically moved with respect to the microbubbles to steer them mechanically. In another embodiment, electronic steering resulting from adjustments to the relative phase of the acoustic energy emitted by the transducer elements is used. The degree of control provided by such electronic steering is inversely proportional to the size of the individual transducer elements 104. For example, it is generally desirable to have the size of the transducer elements be on the order of the wavelength of the acoustic energy emitted by the array, and preferably as small as half the wavelength, in order to effectively steer the ultrasound beams. Thus, with acoustic energy having a wavelength on the order of two millimeters (2 mm), as is often used for focused ultrasound systems, transducer elements having a similar size, i.e., about 2 mm or less in cross-section, would be needed for effective steering. Electronic steering is preferred since physical movement of the transducer array is not required and steering occurs quickly.

Figure 7:
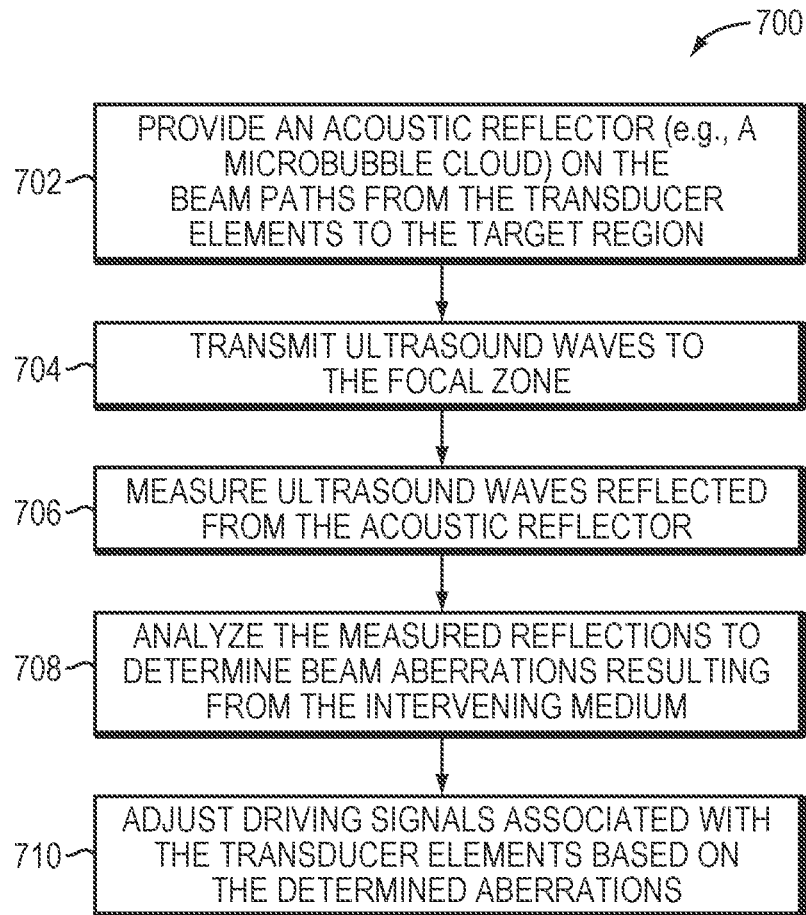
FIG. 7 is a flow chart illustrating an approach for measuring aberrations of ultrasound waves when travelling through a medium and adjusting transducer parameters to compensate for the aberrations in accordance with various embodiments.

FIG. 7 is a flow chart illustrating an approach for measuring ultrasound beam aberrations when traversing a medium located between the transducer and target region and adjusting transducer parameters to compensate for the measured aberrations in accordance with various embodiments. In a first step 702, an acoustic reflector (e.g., a microbubble cloud) is provided on the beam paths from the transducer elements to the target region. The microbubble cloud may be generated by emitting ultrasound waves having an intensity above a threshold and/or introduced from an administration device. In addition, the location, configuration, and/or spanning area of the microbubble cloud may be manipulated and optimized to reflect the ultrasound waves from multiple transducer elements while avoiding microbubble cavitation or other non-linear behavior. Manipulation of the microbubble cloud 602 can be performed by using an acoustic radiation force created by the ultrasound waves and/or a stress created by an ultrasound steering beam. In a second step 704, the transducer elements transmit ultrasound waves to the target region. In a third step 706, ultrasound reflected from the microbubble cloud is measured using the transducer elements 104 and/or acoustic-signal detection device 210. In a fourth step 708, the controller 108 analyzes the measured reflections to determine beam aberrations (e.g., phase shifts) caused by the medium located between the transducer elements and the microbubble cloud. In a fifth step 710, the controller 108 causes the beamformer 106 to adjust drive signals to the transducer elements so as to compensate for the determined aberrations, thereby generating a high-quality focus at the target region 101.

It should be noted that although the transducer-calibration procedure and aberration-compensation procedure described herein utilize microbubbles to reflect ultrasound waves, the ultrasound waves may be reflected using other approaches. For example, the administration system 604 may administer emulsions and/or droplets composed of various liquid perfluorocarbon agents into the target region prior to and/or during the treatment. Initial application of the ultrasound pulses may cause the droplets to vaporize into microbubbles, and subsequent application of the ultrasound pulses may be reflected from the microbubbles. The reflections may be detected and analyzed as described above.

In general, functionality as described above (e.g., analyzing reflected waves to obtain information, such as amplitudes and/or phases associated therewith, comparing the phases of the measured reflections to the expected phases, computing the "time of flight" of the ultrasound waves, estimating the speed of ultrasound waves traversing the medium located between the transducer and the acoustic reflector, comparing the phases of the measured reflections to the phases of the transmitted waves, determining optimal parameters associated with the transducer elements, and/or determining the optimal location of the acoustic reflector) whether integrated within a controller of the imaging system 612, the acoustic-signal detection device 210 and/or an ultrasound system 100, or provided by a separate external controller or other computational entity or entities, may be structured in one or more modules implemented in hardware, software, or a combination of both. For embodiments in which the functions are provided as one or more software programs, the programs may be written in any of a number of high level languages such as PYTHON, JAVA, C, C++, C#, BASIC, various scripting languages, and/or HTML. Additionally, the software can be implemented in an assembly language directed to the microprocessor resident on a target computer (e.g., the controller); for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for focusing an ultrasound transducer comprising a plurality of transducer elements on a target region, the system comprising:
   an acoustic reflector configured to span an area in an intervening medium through which ultrasound waves from the transducer travel; and
   a controller configured to:
       cause at least some of the transducer elements to transmit the ultrasound waves to the target region;
       cause measurements to be made of reflections of the ultrasound waves off the acoustic reflector; and
       based at least in part on the reflection measurements, adjust parameter values associated with said at least some transducer elements so as to compensate for beam aberrations resulting from the intervening medium,
   wherein the area spanned by the acoustic reflector is traversed by a plurality of beam paths of ultrasound waves transmitted from at least some of the transducer elements to the target region.

2. The system of claim 1, further comprising an administration device for an exogenous agent, wherein microbubbles in the exogenous agent form the acoustic reflector.

3. The system of claim 2, wherein the administration device comprises:
   an introducing device for delivering the exogenous agent into the intervening medium; and
   an actuation mechanism for dispensing the exogenous agent from the introducing device;
   wherein the controller is further configured to control activation and deactivation of the actuation mechanism.

4. The system of claim 3, wherein the introducing device comprises at least one of a needle or a catheter.

5. The system of claim 3, wherein the actuation mechanism comprises at least one of a syringe or a peristaltic pump.

6. The system of claim 1, wherein the controller is further configured to cause the transducer elements to transmit ultrasound waves so as to generate microbubbles that form the acoustic reflector.

7. The system of claim 1, wherein the parameter values comprise at least one of frequencies, phases, or amplitudes of signals driving said at least some transducer elements.

8. The system of claim 1, wherein the reflections of the ultrasound waves are measured by said at least some transducer elements.

9. The system of claim 1, further comprising an acoustic-signal detection device for measuring the reflections of the ultrasound waves.

10. The system of claim 1, wherein the acoustic reflector and the ultrasound transducer have complementary contoured shapes.

11. The system of claim 1, wherein the ultrasound transducer and the acoustic reflector have concentric spherical shapes.

12. The system of claim 1, wherein the acoustic reflector and the ultrasound transducer have different contoured shapes.

13. A method of focusing an ultrasound transducer comprising a plurality of transducer elements on a target region, the method comprising:
   providing an acoustic reflector configured to span an area in an intervening medium through which ultrasound waves from the transducer travel;
      causing at least some of the transducer elements to transmit the ultrasound waves to the target region;
      measuring reflections of the ultrasound waves off the acoustic reflector; and
      based at least in part on the reflection measurements, adjusting parameter values associated with said at least some transducer elements so as to compensate for beam aberrations resulting from the intervening medium,
   wherein the area spanned by the acoustic reflector is traversed by a plurality of beam paths of ultrasound waves transmitted from at least some of the transducer elements to the target region.

14. The method of claim 13, further comprising introducing an exogenous agent to the intervening medium, wherein microbubbles in the exogenous agent form the acoustic reflector.

15. The method of claim 13, further comprising causing the transducer elements to transmit ultrasound waves so as to generate microbubbles that form the acoustic reflector.

16. The method of claim 13, wherein the parameter values comprise at least one of frequencies, phases, or amplitudes of signals driving said at least some transducer elements.

17. The method of claim 13, wherein the reflections of the ultrasound waves are measured by said at least some transducer elements.

18. The method of claim 13, wherein the reflections of the ultrasound waves are measured by an acoustic-signal detection device.

19. The method of claim 13, wherein the acoustic reflector and the ultrasound transducer have complementary contoured shapes.

20. The method of claim 13, wherein the ultrasound transducer and the acoustic reflector have concentric spherical shapes.

21. The method of claim 13, wherein the acoustic reflector and the ultrasound transducer have different contoured shapes.

* * * * *